(12) United States Patent
Metelski (10) Patent No.: US 9,394,223 B2
(45) Date of Patent: Jul. 19, 2016

(54) OXIDATION PROCESS FOR PREPARING PURIFIED AROMATIC CARBOXYLIC ACIDS

(71) Applicant: BP Corporation North America Inc., Naperville, IL (US)

(72) Inventor: Peter Metelski, Lisle, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 14/586,085

(22) Filed: Dec. 30, 2014

(65) Prior Publication Data

US 2015/0183705 A1 Jul. 2, 2015

Related U.S. Application Data

(60) Provisional application No. 61/922,308, filed on Dec. 31, 2013.

(51) Int. Cl.
*C07C 51/265* (2006.01)
*C07C 51/487* (2006.01)
*C07C 51/42* (2006.01)
*C07C 51/43* (2006.01)

(52) U.S. Cl.
CPC .............. *C07C 51/487* (2013.01); *C07C 51/265* (2013.01); *C07C 51/42* (2013.01); *C07C 51/43* (2013.01)

(58) Field of Classification Search
CPC ........................... C07C 51/265; C07C 51/487
USPC .................................................. 562/412, 416
See application file for complete search history.

(56) References Cited

U.S. PATENT DOCUMENTS

| 4,081,464 | A | 3/1978 | Marsh et al. |
| 5,760,288 | A | 6/1998 | Asahi et al. |
| 2004/0110980 | A1 | 6/2004 | Sheppard et al. |

FOREIGN PATENT DOCUMENTS

| IT | WO 0206200 A1 * | 1/2002 | ............ C07C 51/487 |
| JP | 03130247 | 6/1991 | |
| JP | 09104653 | * 4/1997 | .............. C07C 63/26 |
| JP | 09151160 | * 6/1997 | .............. C07C 63/26 |
| WO | WO-0206200 | 1/2002 | |
| WO | WO-0206200 A1 * | 1/2002 | ............ C07C 51/265 |
| WO | WO-2008137491 | 11/2008 | |
| WO | WO-2009134872 | 11/2009 | |

* cited by examiner

*Primary Examiner* — Kamal Saeed
*Assistant Examiner* — Janet L Coppins
(74) *Attorney, Agent, or Firm* — Robert N. Carpenter (57) ABSTRACT

A process including: (a) contacting an aqueous solution including a crude aromatic carboxylic acid with an oxygen source in the presence of an oxidation catalyst including at least one of Ru, Au, Pt, Ir or V, and oxides, alloys, salts and mixtures thereof; and (b) purifying the product of step (a) to form a purified aromatic carboxylic acid.

13 Claims, 4 Drawing Sheets

OXIDATION PROCESS FOR PREPARING PURIFIED AROMATIC CARBOXYLIC ACIDS

CROSS-REFERENCE TO RELATED APPLICATIONS

This application claims the benefit of U.S. Provisional Application No. 61/922,308, filed Dec. 31, 2013

BACKGROUND

Aromatic carboxylic acids are raw materials for a wide variety of manufactured articles. For example, terephthalic acid (TA) is manufactured world-wide in amounts exceeding 50 million metric tons per year. A single manufacturing plant typically can produce 100,000 to 1,250,000 metric tons of TA per year. Purified TA (PTA) is used, for example, to prepare polyethylene terephthalate (PET), a raw material for manufacturing polyester fibers for textile applications and polyester film and resin for packaging and container applications.

Crude forms of aromatic carboxylic acid product can be produced by the high-pressure exothermic oxidation of a suitable aromatic feedstock compound in a liquid-phase reaction. A source of molecular oxygen is used as the oxidant, and the reaction is catalyzed by one or more catalyst compounds. For example, crude TA (referred to herein as CTA) is produced during the initial oxidation of paraxylene (pX) and contains a predetermined amount of oxidation reaction intermediates and by-products. These oxidation reaction intermediates and by-products are then removed in subsequent purification steps to produce PTA.

In one well known process for producing PTA, the CTA formed from the oxidation of pX includes impurities such as 4-carboxybenzaldehyde (referred to herein as 4-CBA). The CTA is purified by chemically reducing the 4-CBA to p-toluic acid and washing the resulting p-toluic acid from the product to provide PTA. Processes for the production of PTA are disclosed, for example, in U.S. Pat. Nos. 5,723,656, 7,935,844, 7,935,845, and 8,173,834.

The reaction in which an aromatic reactant is initially oxidized to produce a first crude aromatic carboxylic reaction product is conducted under conditions that inadvertently consume some of the reactant materials, a process referred to generally herein as burning. Burning can also take place as the crude aromatic reaction product produced in the primary oxidation step is further purified to produce a purified aromatic carboxylic acid product (for example, PTA). However, most of the burning in the process for producing the purified aromatic carboxylic acid occurs during the initial oxidation step. Burning represents one of the primary variable costs of the process for making a purified aromatic carboxylic acid.

SUMMARY

The present disclosure is directed to a process for making a purified aromatic carboxylic acid from an aromatic feedstock. In this process the aromatic compound is initially oxidized under reaction conditions selected to minimize burning while achieving required yield and purity of the crude aromatic carboxylic acid. An aqueous mixture including the crude aromatic carboxylic acid reaction product resulting from this initial oxidation step is then further oxidized through exposure to an oxygen source in the presence of an oxidation catalyst including at least one of Ru, Au, Pt, Ir or V, and oxides, salts, alloys and mixtures thereof. The product of this further oxidation step has a level of impurities suitable for incorporation into further purification steps (for example, hydrogenation) to make a purified aromatic carboxylic acid.

This multi-step oxidation procedure selectively oxidizes the aromatic compound without unduly increasing burning or byproducts. Conducting the initial oxidation reaction under conditions selected to minimize burning can provide greater operating flexibility, reduce costs and burden incurred in the downstream purification steps, and reduce the overall costs of the process for making the purified aromatic carboxylic acid.

In one embodiment, the present disclosure is directed at a process including: (a) contacting an aqueous solution including a crude aromatic carboxylic acid with an oxygen source in the presence of an oxidation catalyst including at least one of Ru, Au, Pt, Ir or V, and oxides, alloys, salts and mixtures thereof; and (b) purifying the product of step (a) to form a purified aromatic carboxylic acid.

In another embodiment, the present disclosure is directed to a process including:

(a) oxidizing a feedstock including an alkyl aromatic compound to form a first crude aromatic carboxylic acid reaction product;

(b) oxidizing the first crude aromatic carboxylic acid reaction product in one or more sequential reaction mixtures to form a second crude aromatic carboxylic acid reaction product, wherein the second crude aromatic carboxylic acid reaction product includes 3000 ppm by weight (ppmw) to 10,000 ppmw of aldehyde intermediate reaction products;

(c) contacting an aqueous reaction mixture comprising the second crude aromatic carboxylic acid reaction product with an oxygen source in the presence of an oxidation catalyst including at least one of Ru, Au, Pt, Ir and V, and oxides, alloys, salts and mixtures thereof, to form a third crude aromatic carboxylic acid reaction product, wherein the second crude aromatic carboxylic acid reaction product comprises 3000 ppmw to 6,000 ppmw of aldehyde intermediate reaction products; and (d) purifying the third crude aromatic carboxylic acid reaction product with hydrogen to form purified aromatic carboxylic acid, wherein the purified aromatic carboxylic acid has less than 100 ppmw aldehyde intermediate reaction products.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Like symbols in the drawings indicate like elements.

DETAILED DESCRIPTION

According to one embodiment of the present invention, an aromatic feedstock compound is first catalytically oxidized in a primary oxidation reaction. The primary oxidation reaction takes place in a first reaction mixture to produce a first crude aromatic carboxylic acid reaction product. Based on the reaction conditions selected for the primary oxidation reaction, the first crude aromatic carboxylic acid reaction product includes impurities such as, for example, oxidation reaction intermediates and by-products, and catalyst components such as catalyst metals and salts.

The aromatic feedstock compound for the primary oxidation reaction includes any aromatic compound that has substituents on at least one benzene ring that can be oxidized to a carboxylic acid group. For example, in some embodiments the oxidizable substituent can be an alkyl group. In some embodiments, the alkyl group can be, for example, methyl, ethyl, or isopropyl, or a partially oxidized alkyl group such as an alcohol group, aldehyde group or ketone group. The aromatic portion of the aromatic feedstock compound can be a benzene ring, or it can be bi- or polycyclic such as, for example, a naphthalene ring structure.

The number of oxidizable substituents on the aromatic portion of the aromatic feedstock compound can be equal to the number of sites available on the aromatic portion of the aromatic feedstock compound. In some embodiments, the number of oxidizable substituents is about 1 to about 4, or about 2 to about 3. Thus, examples of suitable aromatic feedstock compounds for the process of this disclosure include toluene, ethylbenzene, orthoxylene, metaxylene, paraxylene, 1-formyl-4-methylbenzene, 1-hydroxymethyl-4-methylbenzene, 1,2,4-trimethylbenzene, 1-formyl-2,4-dimethylbenzene, 1,2,4,5-tetramethylbenzene, alkyl, hydroxymethyl, formyl, and acyl substituted naphthalene compounds such as 2,6- and 2,7-dimethylnaphthalene, 2-acyl-6-methylnaphthalene, 2-formyl-6-methylnaphthalene, 2-methyl-6-ethylnaphthalene, 2,6-diethylnaphthalene, and the like.

Paraxylene (pX), for example, when initially oxidized produces crude terephthalic acid (CTA). The CTA includes a number of oxidation reaction intermediates and by-products, including, for example, 4-carboxybenzaldehyde (4-CBA), p-toluic acid, catalysts metals and salts, and the like. As other examples, the initial oxidation of metaxylene produces crude isophthalic acid, while the initial oxidation of 2,6-dimethylnaphthalene produces crude 2,6-naphthalenedicarboxylic acid.

The first reaction mixture used in the primary oxidation reaction includes a first solvent. In some embodiments, the first solvent includes water. In some embodiments, the first solvent includes a low molecular weight aliphatic monocarboxylic acid having 2 to 6 carbon atoms, inclusive, or mixtures thereof, with water. In some embodiments, the aliphatic monocarboxylic acid used in the first oxidation reaction mixture is acetic acid, and the first solvent includes mixtures of acetic acid and water.

In some embodiments, the first reaction mixture includes a promoter such as a low molecular weight ketone having 2 to 6 carbon atoms, or a low molecular weight aldehyde having 1 to 6 carbon atoms. Alternately, bromine promoter compounds such as hydrogen bromide, molecular bromine, sodium bromide and the like can also be used.

The primary oxidation reaction is conducted with a source of molecular oxygen, typically air. For example, in the conversion of pX to crude terephthalic acid (CTA), the source of molecular oxygen can vary in molecular oxygen content from that of 10% molecular oxygen, to pure molecular oxygen gas. Air is the preferred source of molecular oxygen for the first oxidation reaction. The oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen (measured on a solvent-free basis) in the overhead gas-vapor mixture.

The primary oxidation reaction takes place in the presence of a first oxidation catalyst. In some embodiments, the first oxidation catalyst includes a metal. In some embodiments, the primary oxidation catalyst includes at least one of cobalt, manganese, and bromine components, or mixtures and combinations thereof, and can optionally include accelerators such as, for example, polycyclic aromatic promoters such as anthracene, bromide substitutes such as dibromoanthracene, phthalimides, and tetrabromoethane, and metallic promoters known in the art such as Group 4 metals (Hf, Zr) and others (Ni, Ce).

As an example, if the aromatic feedstock compound is pX, the ratio of cobalt (calculated as elemental cobalt) in the cobalt component of the catalyst in the first oxidation reaction is suitably in the range of about 0.2 to about 10 milligram atoms (mga) per gram mole of pX. The ratio of manganese (calculated as elemental manganese) in the manganese component of the catalyst-to-cobalt (calculated as elemental cobalt) in the cobalt component of the catalyst is about 0.2 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the first oxidation reaction is suitably in the range of about 0.2 to about 1.5 mga per mga of total cobalt and manganese.

Each of the cobalt and manganese components in the first reaction mixture can be provided in any of its known ionic or combined forms that provide soluble forms of cobalt, manganese, and bromine in the solvent in the reactor. For example, when the first solvent is an acetic acid medium, cobalt and/or manganese carbonate, acetate tetrahydrate, and/or bromine can be employed. The 0.2:1.0 to 1.5:1.0 bromine-to-total cobalt and manganese milligram atom ratio is provided by a suitable source of bromine. Such bromine sources include elemental bromine ($Br_2$), or ionic bromine (for example HBr, NaBr, KBr, $NH_4Br$, etc.), or organic bromides which are known to provide bromide ions at the operating temperature of the oxidation (e.g. benzylbromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratio of 0.2:1.0 to 1.5:1.0. The bromine ion released from the organic bromides at the oxidation operating conditions in the first oxidation reaction can be readily determined by known analytical techniques.

The primary oxidation reaction can be conducted at a reaction temperature of about 145° C. to about 235° C., and in some embodiments the reaction pressure is maintained such that the first reaction mixture is under liquid phase conditions. For example, for the oxidation of pX to CTA, the minimum pressure at which the oxidation reactor is maintained is typically that pressure which will maintain a substantial liquid phase of the pX and the solvent. When the solvent is an acetic acid-water mixture, suitable reaction gauge pressures in the oxidation reactor are from about 0 kg/cm$^2$ to about 35 kg/cm$^2$, and typically are from about 5 kg/cm$^2$ to about 25 kg/cm$^2$, or from about 7 kg/cm$^2$ to about 21 kg/cm$^2$. The temperature range within the oxidation reactor for the primary oxidation reaction is generally from about 120° C., in some embodiments from about 150° C., to about 240° C., preferably to about 230° C. The solvent residence time in the first oxidation reactor is generally from about 20 to about 150 minutes, and in some embodiments from about 30 to about 120 minutes.

The process conditions described above for oxidizing pX to CTA can also be used to oxidize metaxylene to isophthalic acid. For the oxidation of 2,6-dimethylnaphthalene to 2,6-naphthalenedicarboxylic acid the weight ratio of monocarboxylic acid solvent to 2,6-dimethylnaphthalene is preferably about 2:1 to about 12:1, the mga ratio of manganese to cobalt is about 5:1 to about 0.1:1, the mga ratio of bromine to the total of cobalt and manganese is about 0.3:1 to about 0.8:1 and the total of cobalt and manganese, calculated as elemental cobalt and elemental manganese, is at least about 0.40 weight percent based on the weight of the solvent. The oxidation reaction temperature is about 185° C. to about 220° C. In some embodiments, acetic acid is the solvent for the primary oxidation of 2,6-dimethylnaphthalene.

In some embodiments, the water produced by the condensation of the primary oxidation reactor off-gas can be used as the solvent for a subsequent purification step. For example, the water formed by the condensation from the reaction off-gas can be used as a recrystallization solvent or as a solvent for conducting one or more chemical and/or physical treatments for the first crude aromatic carboxylic acid.

The reaction conditions in the primary oxidation reaction are selected to provide the first crude aromatic carboxylic acid with a predetermined first impurity level. As noted above, in some embodiments, to reduce burning the reaction conditions in the primary oxidation reaction are selected to provide a first impurity level the same or higher than the impurity level of the crude aromatic carboxylic acid reaction product produced by the primary oxidation reaction in a conventional commercial process. In some non-limiting exemplary embodiments, the first crude aromatic carboxylic acid reaction product includes greater than about 3000 ppm by weight (ppmw) of aldehyde intermediate reaction products. In some embodiments, the first crude aromatic carboxylic acid reaction product includes about 3000 ppmw to about 10,000 ppmw of aldehyde intermediate reaction products.

For example, in the first oxidation of pX to CTA, in some embodiments the primary oxidation reaction conditions result in a first crude CTA with an amount of 4-CBA greater than about 3000 ppmw, or about 3000 ppmw to about 10,000 ppmw.

Using the oxidation of pX to CTA as an example, to reduce the severity of the primary oxidation reaction and provide a first crude CTA impurity level greater than about 3000 ppmw and up to about 10,000 ppmw, any or all of the following reaction conditions could be adjusted in the primary oxidation reactor (this listing is provided as an example and is not intended to be limiting):

Temperature and pressure in the reactor: higher temperatures and pressures result in higher conversion of 4-CBA to TA, and higher burning of the pX and solvent, and in some embodiments decreasing temperature and pressure can result in lower conversion of 4-CBA to TA and lower burning.

Vent O$_2$: In some embodiments, oxygen is fed stoichiometrically to the primary oxidation reactor (about 3 eq O$_2$ per 1 eq pX), and a slight excess is added to drive the reaction to high conversion of pX to CTA (about 3.5 eq O$_2$). A large excess of oxygen (greater than about 4 eq.) will result in combustion of solvent (for example, acetic acid) and pX to form CO$_x$. Vent O$_2$ can be changed either by increasing or decreasing the air flow to the primary oxidation reactor, or by increasing or decreasing pX flow to the primary oxidation reactor. In some embodiments, lowering vent O$_2$ can reduce the severity of the primary oxidation reaction.

Water Concentration: Water is created as a byproduct of the oxidation of pX and moderates the reaction and makes the primary oxidation less severe by cooling the reaction and (slightly) deactivating the first catalyst. In some embodiments, the first solvent will be 80-90% acetic acid and 10-20% water. If the primary oxidation reaction is dryer (less than about 10% water), the reaction becomes more severe and CO$_x$ increases, while 4-CBA decreases. If the primary oxidation reaction is wetter (greater than about 20% water) then the temperature drops and the catalyst deactivates; 4-CBA goes up and CO$_x$ goes down, so increasing water concentration in the first reaction mixture can lower the conversion of 4-CBA to TA and reduce burning in the primary oxidation reaction.

Catalyst concentration: The overall catalyst (for example, CoMnBr) concentration, as well as concentration of the individual catalyst components (Co, Mn, Br) affect the severity of the primary oxidation reaction. In general, high catalyst concentration increases conversion of 4-CBA to pX while increasing burning. Some catalyst is lost during recycle and must be made up by purchasing new catalyst from specialty manufacturers. Also, the catalyst can be corrosive and costs are incurred in the maintenance of the plant due to corrosion. In some embodiments, costs are incurred to ensure that catalyst does not contaminate air, land and water. Reducing catalyst usage is of great benefit, and in some embodiments reduced catalyst in the primary oxidation reaction can reduce conversion of 4-CBA and burning.

In a second step of the process, a slurry including the first crude carboxylic acid reaction product exits the first oxidation reactor and is directed to at least one crystallizer, typically a sequence of crystallizers, where the slurry is gradually cooled to crystallize dissolved crude aromatic carboxylic acid. At least one of the crystallizers may optionally include an air sparger to further oxidize the first crude aromatic carboxylic acid reaction product to a second crude aromatic carboxylic acid reaction product. The optional one or a sequence of oxidation steps conducted in the crystallizers is referred to generally herein as the secondary oxidation reaction. The secondary oxidation reaction, if any, takes place in the crystallizers in a sequence of second reaction mixtures that may be the same or different from the first oxidation reaction mixture.

In some non-limiting exemplary embodiments, the second crude aromatic carboxylic acid reaction product includes greater than about 3000 ppm by weight (ppmw) of aldehyde intermediate reaction products. In some embodiments, the second crude aromatic carboxylic acid reaction product includes about 3000 ppmw to about 10,000 ppmw of aldehyde intermediate reaction products. For example, in the first oxidation of pX to CTA, in some embodiments the primary and secondary oxidation reaction conditions result in a second CTA with an amount of 4-CBA greater than about 3000 ppmw, or about 3000 ppmw to about 10,000 ppmw.

The slurry including the first crude aromatic carboxylic acid reaction product and any second crude aromatic carboxylic acid reaction product(s) (referred to herein for simplicity as the second crude aromatic carboxylic acid reaction product) is incorporated into a third reaction mixture that is different from the first and the second reaction mixtures, and then further catalytically oxidized in a tertiary oxidation step.

The reaction conditions for the tertiary oxidation step result in a third crude aromatic carboxylic reaction product with a level of impurities such as, for example, oxidation reaction intermediates and by-products, catalyst components, and the like. In some non-limiting exemplary embodiments, the third crude aromatic carboxylic acid reaction product includes about 3000 ppmw to about 6,000 ppmw of aldehyde intermediate reaction products, or about 3000 ppmw to about 4,000 ppmw of aldehyde intermediate reaction products. For example, the first and any second CTA produced in the primary and optional secondary catalytic oxidations of pX can be further oxidized in the tertiary oxidation reaction to produce a third CTA that includes a lower level of oxidation reaction intermediates and by-products, including, for example, 4-CBA, compared to the first and second CTAs. In some exemplary, non-limiting embodiments, the amount of 4-CBA in the third CTA provides an input stream that is suitable for economical purification procedures (for example, hydrogenation) in which the third CTA is purified to form PTA. In some embodiments, the amount of 4-CBA in the third CTA is about 3000 ppmw to about 6000 ppmw, or about 3000 ppmw to about 4000 ppmw.

The tertiary catalytic oxidation reaction takes place in a third reaction mixture that is different from the first and the second reaction mixtures used in the primary and secondary oxidation reactions. In some embodiments, the tertiary oxidation reaction takes place at higher temperatures and pressures than the primary and secondary oxidation reactions.

The third oxidation reaction mixture includes a third solvent that is capable of at least partially solubilizing, or dissolving, the first and any second crude aromatic carboxylic reaction products and to obtain a substantially homogeneous solution. The first and any second crude aromatic carboxylic acid reaction products may be solubilized or dissolved in the third solvent with optional heating and pressure. In some embodiments, the third solvent includes water, and in some embodiments the third solvent is water.

The tertiary oxidation reaction is also conducted in the presence of an oxygen source, which in some embodiments can be provided by commercially available peroxides (for example, hydrogen peroxide ($H_2O_2$)), air, molecular oxygen, $O_2$-enriched air, or mixtures thereof.

For example, in the conversion of pX to CTA, air or peroxide is supplied to the tertiary oxidation reactor in sufficient quantity to oxidize the residual 4-CBA in the CTA to about 3000 ppmw to about 6000 ppmw, or about 3000 ppmw to about 4000 ppmw, which is suitable for introduction into conventional subsequent purification steps in which the third CTA is purified to form PTA. In some embodiments, the third reaction mixture can include sources of aqueous $H_2O_2$ containing about 0.1 wt % $H_2O_2$ to about 50 wt % $H_2O_2$, or about 1 wt % to about 5 wt %, or about 2 wt % to about 4 wt % added in sufficient quantity to reduce the residual 4-CBA to a desired level. In some embodiments, the third oxidation reaction mixture can include about 1 to about 100 equivalents $H_2O_2$, or about 0.5 to about 50 equivalents of oxygen, per equivalent of 4-CBA.

The third reaction mixture is fed into a tertiary oxidation reactor including a third oxidation catalyst different from the first and second oxidation catalysts. The third oxidation catalyst can include any catalyst metal or combination of catalyst metals that effectively converts the oxidation intermediates and by-products in the first and any second crude aromatic carboxylic acid reaction products without significantly adding to burning of reactants or creating further unwanted by-products. For example, in the oxidation of pX to CTA, the third oxidation catalyst should be selected to effectively convert 4-CBA without excess burning of reactant materials or production of benzoic acid.

In some embodiments, the third oxidation catalyst includes at least one element selected from Groups 5, 8, 9, 10, or 11 of the Periodic Table, as well as oxides, salts and alloys thereof. In some embodiments, the third oxidation catalyst includes least one metal selected from Ru, Au, Pt, Ir and V, as well as oxides, salts and alloys thereof.

In some embodiments, the third oxidation catalyst can be a homogeneous catalyst system including at least one of Ru, Au, Pt, Ir, or V, as well as oxides, salts and alloys thereof. In other embodiments, the third oxidation catalyst can be a heterogeneous catalyst system including Ru, Au, Pt, Ii, or V and another metal, as well as oxides, salts and alloys thereof. In some embodiments, the heterogeneous catalyst system includes at least one of the following: Ru and at least one of Ge, Nb, Mo, In, Au, Sn, Sb, Fe, Ti, Ag, Ta, W, Bi, Re, Pb, Sc, Cr, Ce or Te, as well as oxides, salts and alloys thereof; Au and at least one of Sc, Ta or Cu, Pt and Te, as well as oxides, salts and alloys thereof; Ir and at least one of Ce, Co or V, as well as oxides, alloys and salts thereof; or V and at least one of Nb, Ge, or Ga, as well as oxides, salts and alloys thereof.

Any of the catalyst metals utilized in the tertiary oxidation reaction can optionally be supplied on a support, which may or may not be inert. Suitable supports for the third oxidation catalysts include, but are not limited to, alumina, ceria, silica, zirconia, titania, silicon carbide, carbon, and combinations thereof. In some embodiments, the supports include carbon (C) and rutile ($TiO_2$). The catalyst system used in the tertiary oxidation reaction may be provided as a fixed or a fluidized bed.

For example, in some embodiments suitable for converting 4-CBA as pX is oxidized to CTA, the third oxidation catalyst can include at least one of the following: ruthenium on a carbon support (Ru/C), as well as oxides, salts and alloys thereof; ruthenium on a rutile support (Ru/rutile), as well as oxides, salts and alloys thereof; Ru/rutile and Sb, as well as oxides, salts and alloys thereof; Ru/rutile and at least one of Mo and Pb, as well as oxides, salts and alloys thereof; Ru/rutile and at least one of Mo and In, as well as oxides, salts and alloys thereof; Ru/C and at least one of In and Au, as well as oxides, salts and alloys thereof; or Ru/rutile and at least one of Mo and Nb, as well as oxides, salts and alloys thereof.

In some embodiments, non-limiting examples of the catalyst for the tertiary oxidation reaction can include ruthenium metal, ruthenium acetate, ruthenium chloride, ruthenium bromide, ruthenium iodide, ruthenium acetylacetonate, ruthenium oxide, ruthenium nitrate, hexaammine ruthenium chloride, and mixtures thereof. The ruthenium-containing catalyst can be mounted on a solid support such as alumina, ceria, zirconia, silica, titania or mixtures thereof.

In other non-limiting embodiments, the ruthenium-containing catalyst for the tertiary oxidation reaction can further include molybdenum chloride, molybdenum acetate, molybdenum oxide, molybdenum sulfide, molybdenum disilicide, molybdenum carbide, molybdenum boride, molybdenum hexacarbonyl, molybdate salts, gallium metal, gallium iodide, gallium acetylacetonate, gallium chloride, gallium bromide, gallium fluoride, gallium oxide, gallium nitride, gallium phosphide, gallium arsenide, gallium nitrate, gallium sulfate, gallium sulfide, gallium perchlorate, trimethylgallium, triethylgallium, indium metal, indium fluoride, indium chloride, indium bromide, indium iodide, indium oxide, indium nitride, indium nitrate, indium phosphide, indium selenide, indium antimonide, indium acetate, indium acetylacetonate, indium trifluoromethanesulfonate, indium sulfide, indium sulfate, indium hydroxide, and mixtures thereof.

As an example, if the aromatic feedstock compound is pX, the ratio of Ru in the third oxidation reaction is suitably in the range of about 0.2 to about 10 milligram atoms (mga) per gram mole of pX.

In various embodiments, the tertiary oxidation reaction is conducted at a temperature of about 200° C. to about 400° C., or about 250° C. to about 300° C., or about 285° C. to about 295° C. In various embodiments, the tertiary oxidation reaction is conducted under a pressure in the tertiary oxidation reactor of about 200 psi to about 1500 psig, or about 500 psig to about 1400 psig, or about 1000 psig to about 1300 psig.

In some embodiments, the tertiary oxidation reaction is conducted in the tertiary oxidation reactor under an oxygen-reduced or inert atmosphere. For example, the second oxidation reaction may be conducted under a blanket of nitrogen, carbon dioxide or argon.

The third crude aromatic carboxylic acid reaction product produced in the tertiary oxidation step is further purified to form a purified aromatic carboxylic acid. In the purification procedure, one or more chemical and/or physical treatments are performed on the crude aromatic carboxylic acid from the tertiary oxidation step to further reduce the impurity level thereof. In some embodiments, one such purification process includes contacting an aqueous solution or slurry of the crude aromatic carboxylic acid with hydrogen at an elevated temperature and pressure in the presence of a hydrogenation catalyst.

Using the purification of CTA as an example, this purification procedure is conducted at an elevated temperature and pressure in a fixed catalyst bed. Both down-flow and up-flow reactors can be used. The CTA to be purified is dissolved in water or a mixture of water and some other polar solvent such as a $C_1$-$C_4$ aliphatic carboxylic acid. The reactor, and thus the CTA solution temperature during purification, can be about 100° C. to about 350° C., or about 275° C. to about 300° C.

Reactor pressure conditions in the purification step primarily depend upon the temperature at which the purification process is carried out. Inasmuch as the temperatures at which practical amounts of the impure aromatic carboxylic acid may be dissolved are substantially above the normal boiling point of the solvent, the process pressures are typically above atmospheric pressure to maintain the aqueous solutions in liquid phase. In general, the reactor pressure during hydrogenation can be in the range of about 200 to about 1500 pounds per square inch gauge (psig), and usually is in the range of about 900 psig to about 1,300 psig. The hydrogen partial pressure is typically in the range of about 30 psig to about 200 psig.

The catalyst used for this purification step comprises one or more active hydrogenation metals such as Ru, Rh, Pd or Pt, or combinations thereof, on a suitable support such as carbon or titania.

After passing through the reactor for purifying the crude aromatic carboxylic acid, the solution of aromatic carboxylic acid in aqueous solvent is cooled to precipitate the purified aromatic carboxylic acid. The temperature to which the solution is cooled is such that most of the purified aromatic carboxylic acid crystallizes. The crystallized purified aromatic carboxylic acid is separated from the aqueous mother liquor using a suitable solid-liquid separation device such as a centrifuge or filter. The cake of purified aromatic carboxylic acid can be washed with pure water, dried and sent to storage or for packaging and shipment.

The purified aromatic carboxylic acid includes less than 200 ppmw of aldehyde intermediate reaction products, or less than 150 ppmw, or less than 100 ppmw, or about 5 ppmw to about 25 ppmw of aldehyde intermediate reaction products. For example, purified PTA includes less than 200 ppmw of 4-CBA, less than 150 ppmw, or less than 100 ppmw, or about 5 ppmw to about 25 ppmw of 4-CBA.

Figure 1:
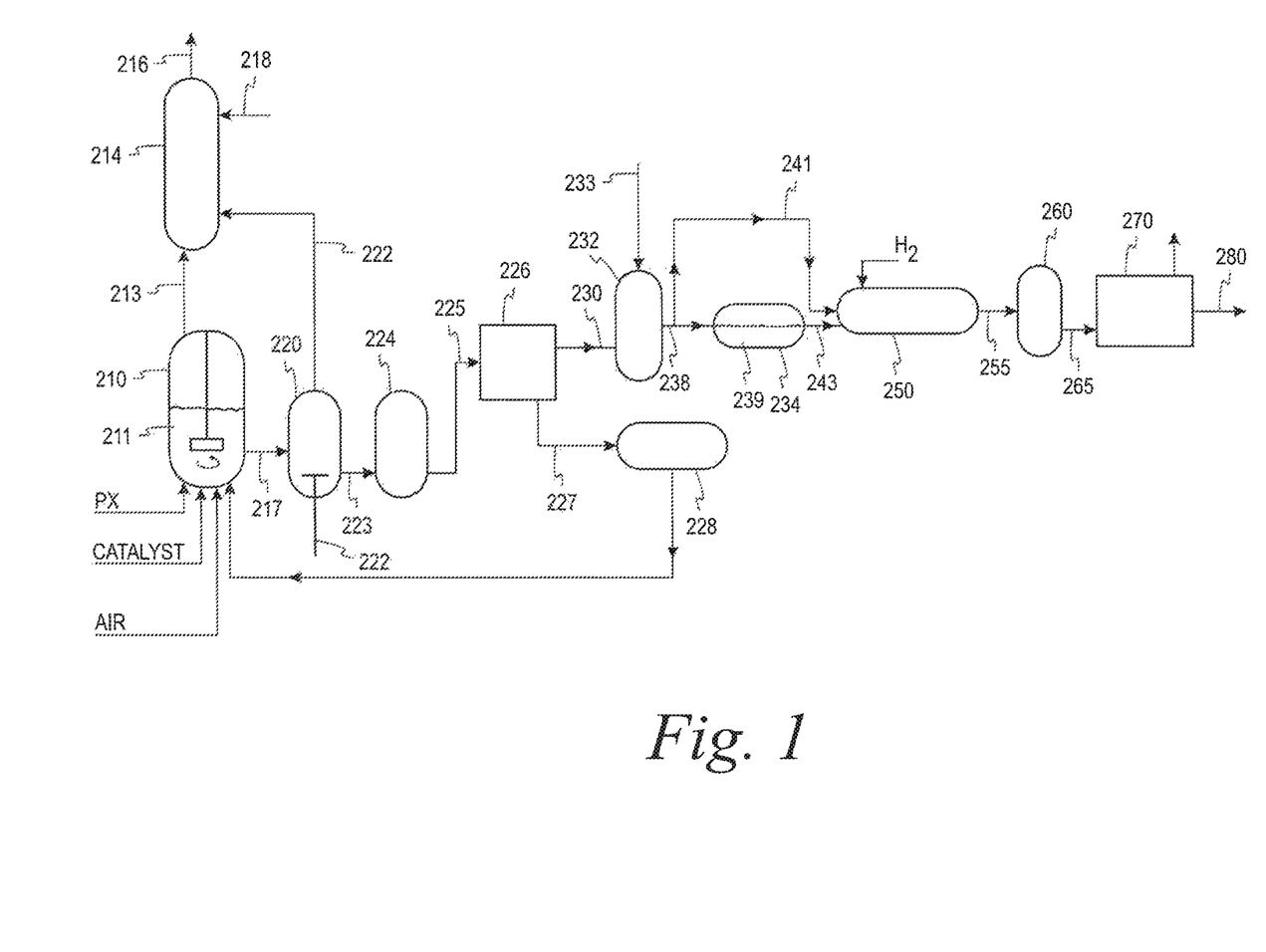
FIG. 1 is a flow diagram of a system that can be used to carry out an embodiment of the process of the present disclosure.

FIG. 1 is a schematic diagram of an embodiment of a system for operating a multi-step oxidation process of this disclosure for converting the aromatic feedstock compound paraxylene (pX) to purified terephthalic acid (TA). In an agitated oxidation reactor 210, pX is reacted with air in a first reaction mixture 211. In some embodiments, the first reaction mixture 211 includes an aqueous solvent, which optionally includes a carboxylic acid such as, for example, acetic acid.

The first reaction mixture 211 includes a first oxidation catalyst. In some embodiments, the first oxidation catalyst includes cobalt and manganese metals and one or more optional bromine compounds such as hydrogen bromide as an optional oxidation promoter. In some embodiments, the first oxidation reaction is conducted at a temperature of about 170° C. to about 210° C., and at a pressure of about 7 to about 21 kg/cm$^2$.

The heat generated by the exothermic primary oxidation reaction causes the first reaction mixture 211 to boil. The heat generated during the primary oxidation reaction is dissipated by allowing the reaction solvent to vaporize from the first reaction mixture 211. The high temperature, high pressure vapor generated by the liquid phase primary oxidation reaction is a significant source of energy. In some embodiments, the vaporized reaction solvent from the primary oxidation reaction is directed in a line 213 to an apparatus 214, such as a high pressure distillation column, that can separate the solvent, typically a low molecular weight aliphatic carboxylic acid, from the water produced during the first oxidation reaction.

An off-gas containing steam and exiting column 214 via line 216 may be further processed. For example, the steam may be condensed and the condensate used as reflux 218 for the distillation column 214. Incondensible gases remaining after condensation may be treated to remove impurities. The steam may also be directed to an expander connected to an electric generator and/or to other equipment requiring mechanical work such as a compressor. The electrical energy produced by the generator can be used to, for example, power the equipment used in the plant for manufacturing the purified aromatic carboxylic acid, or to operate compressors for adding air to the first oxidation reaction mixture. Any excess electrical energy can be transmitted to a local electric power utility. Examples of further processing of the off-gas and reflux options for the column 214 are described, for example, in U.S. Pat. Nos. 5,723,656, 6,137,001, 7,935,844, 7,935,845, and 8,173,834.

A slurry including a first crude carboxylic reaction product (CTA) with a first impurity level (water, acetic acid, catalyst metals, and reaction intermediates and by-products from the primary oxidation reaction such as 4-carboxybenzaldehyde (4-CBA)) exits the oxidation reactor 210 through a line 217 and is directed to vessel 220 where the temperature of the first reaction mixture 211 is optionally reduced to crystallize dissolved terephthalic acid (TA). The vessel 220 is optionally equipped with an air sparger 222 to create a secondary oxidation reaction, which in some embodiments reduces the 4-CBA concentration in the CTA, for example, to a concentration in the range of about 3000 ppmw to about 10,000 ppmw. The second CTA from the vessel 220 is directed to a vessel 224 through a line 223 wherein additional cooling and crystallization of TA occurs, and the CTA may be further oxidized.

A slurry including the second CTA from the vessel 224 enters a separation apparatus 226 through a line 225. The separation apparatus 226 is typically one or more centrifuges, a rotary vacuum filter or a pressure filter. In one particular embodiment, the separation apparatus 226 is a pressure filter adapted for solvent exchange by positive displacement under pressure of mother liquor in a filter cake with wash liquid including water. Such a method is described, for example, in U.S. Pat. No. 5,200,557. In the separation apparatus 226, the second CTA is separated from the oxidation reaction mother liquor.

The oxidation reaction mother liquor exits the separation apparatus 226 through a line 227 and enters a mother liquor drum 228. A major portion of the mother liquor containing catalyst and the solvent from the oxidation reactions is recycled to the first oxidation reactor 210 through a line 229.

A slurry of the second CTA and water exits the separation apparatus through a line 230 and enters a slurry drum 232 and is mixed with a reaction solvent fed from line 233 to form a reaction mixture in the slurry drum 232. The reaction mixture exits the slurry drum 232 through a line 237 to a tertiary oxidation reactor 234. This third oxidation reaction mixture 239 is different in composition from the first oxidation reaction mixture 211 and the second reaction mixture utilized in the secondary oxidation in the crystallization vessel 220. The tertiary oxidation reaction forms a tertiary crude carboxylic reaction product (CIA) with a third impurity level less than the first impurity level in the first CIA and the second impurity level in the second CTA. In some embodiments, the tertiary oxidation step further reduces the 4-CBA concentration in the CTA to about 3000 ppmw to about 6,000 ppmw or to about 3000 ppmw to about 4000 ppmw.

The solvent 233 may be selected from any solvents suitable for solubilizing the first and any second CTA. In some embodiments, the third solvent is aqueous, and in some embodiments the third solvent is water.

The tertiary oxidation reactor 234 also includes an oxygen source (not shown), which in some embodiments can be provided by peroxides (especially hydrogen peroxide ($H_2O_2$)), air, molecular oxygen, and combinations thereof.

The tertiary oxidation reaction mixture 239 also includes a third oxidation catalyst different from the first and second oxidation catalysts used in the primary and secondary oxidation steps. The third oxidation catalyst can include any catalyst metal or combination of catalyst metals that effectively reduces the level of oxidation intermediates and by-products in the first or any second crude aromatic reaction products without significantly adding to burning or production of further unwanted by-products. In this embodiment, the catalyst selected for the tertiary oxidation reaction should effectively convert and reduce the amount of 4-CBA in the first or any second CTA without excess burning of reactant materials or production of by-products such as benzoic acid.

In some embodiments, the third oxidation catalyst includes at least one element selected from Groups 5, 8, 9, 10, or 11 of the Periodic Table, as well as oxides, salts, alloys and mixtures thereof. In some embodiments, the third oxidation catalyst includes least one metal selected from Ru, Au, Pt, Ir and V, as well as oxides, salts, alloys and mixtures thereof.

In some embodiments, the third oxidation catalyst can be a homogeneous catalyst system including at least one of Ru, Au, Pt, Ir, or V, as well as oxides, salts, alloys and mixtures thereof. In other embodiments, the third oxidation catalyst can be a heterogeneous catalyst system including Ru, Au, Pt, Ir, or V and another metal, as well as oxides, salts, alloys and mixtures thereof. In some embodiments, the heterogeneous catalyst system includes at least one of the following: Ru and at least one of Ge, Nb, Mo, In, Au, Sn, Sb, Fe, Ti, Ag, Ta, W, Bi, Re, Pb, Sc, Cr, Ce or Te, as well as oxides, salts, alloys and mixtures thereof; Au and at least one of Sc, Ta or Cu, Pt and Te, as well as oxides, salts, alloys and mixtures thereof; Ir and at least one of Ce, Co or V, as well as oxides, salts, alloys and mixtures thereof; or V and at least one of Nb, Ge, or Ga, as well as oxides, salts, alloys and mixtures thereof.

Any of the catalyst metals utilized in the third oxidation reaction can optionally be supplied on a support, which may or may not be inert. Suitable supports for the third oxidation catalysts include, but are not limited to, alumina, silica, zirconia, titania, silicon carbide, carbon, and combinations thereof. In some embodiments, the supports include carbon (C) and rutile ($T_iO_2$).

For example, in some embodiments suitable for converting 4-CBA as pX is oxidized to CTA, the third oxidation catalyst can include at least one of the following: ruthenium metal on a carbon support (Ru/C), as well as oxides, salts, alloys and mixtures thereof; ruthenium on a rutile support (Ru/rutile), as well as oxides, salts, alloys and mixtures thereof; Ru/rutile and Sb, as well as oxides, salts, alloys and mixtures thereof; Ru/rutile and at least one of Mo and Pb, as well as oxides, salts, alloys and mixtures thereof; Ru/rutile and at least one of Mo and In, as well as oxides, salts, alloys and mixtures thereof; Ru/C and at least one of In and Au, as well as oxides, salts, alloys and mixtures thereof; and Ru/rutile and at least one of Mo and Nb, as well as oxides, salts, alloys and mixtures thereof.

In other non-limiting examples, the third oxidation catalyst for converting 4-CBA as pX to CTA can include ruthenium metal, ruthenium acetate, ruthenium chloride, ruthenium bromide, ruthenium iodide, ruthenium acetylacetonate, ruthenium oxide, ruthenium nitrate, hexaammine ruthenium chloride. The ruthenium metal may be mounted on a solid support such as alumina, ceria, zirconia, silica, titania or mixtures thereof.

In further non-limiting examples, the third oxidation catalyst for converting 4-CBA as pX to CTA can include an oxide, salt or alloy of ruthenium, along with molybdenum chloride, molybdenum acetate, molybdenum oxide, molybdenum sulfide, molybdenum disilicide, molybdenum carbide, molybdenum boride, molybdenum hexacarbonyl, molybdate salts, gallium metal, gallium iodide, gallium acetylacetonate, gallium chloride, gallium bromide, gallium fluoride, gallium oxide, gallium nitride, gallium phosphide, gallium arsenide, gallium nitrate, gallium sulfate, gallium sulfide, gallium perchlorate, trimethylgallium, triethylgallium, indium metal, indium fluoride, indium chloride, indium bromide, indium iodide, indium oxide, indium nitride, indium nitrate, indium phosphide, indium selenide, indium antimonide, indium acetate, indium acetylacetonate, indium trifluoromethanesulfonate, indium sulfide, indium sulfate, indium hydroxide, and alloys and mixtures thereof.

The third oxidation reaction mixture 239 is maintained at a temperature of about 200° C. to about 400° C., or about 250° C. to about 300° C. The tertiary oxidation reaction is conducted under a pressure of about 200 psig to about 1500 psig, or about 500 psig to about 1400 psig, or about 1000 psig to about 1300 psig. In some embodiments, the tertiary oxidation reactor 234 includes an oxygen-reduced or inert atmosphere.

Depending on the reaction conditions selected for the primary, optional secondary, and third oxidation reactions, and the resulting impurity level in the first CTA relative to the resulting impurity level in the second CTA, a portion (or all) of the second CTA from the slurry drum 232 may optionally by-pass the tertiary oxidation reactor 234 in the by-pass line 241 to enter a downstream hydrogenation reactor 250. The third CTA from the tertiary oxidation reaction in the reactor 234 enters the hydrogenation reactor 250 in the line 243.

In the hydrogenation reactor 250, the CTA is treated with hydrogen at an elevated temperature, for example, about 260° C. to about 290° C., and elevated pressure to purify the CTA(s) by, for example, further reducing the levels of 4-CBA or other impurities.

The reaction product from the hydrogenation reactor 250, which in this embodiment is a PTA, enters a crystallization vessel 260 through a line 255. The slurry of PTA and water formed in the crystallization vessel 260 is directed to a separation apparatus 270 through a line 265. The separation apparatus 270 is generally a centrifuge, a rotary vacuum filter, or a pressure filter. Mother liquor from the separation apparatus 270 that includes water, acetic acid, dissolved and suspended purified terephthalic acid (PTA), and various intermediate and by-product compounds, may optionally be recycled to the top of the high pressure distillation column 214 through a line 275. PTA exits the separation apparatus 270 through a line 280. In some embodiments, the PTA includes less than about 100 ppmw of 4-CBA, or about 5 ppmw to about 25 ppmw of 4-CBA.

The PTA may be further processed to produce polyethylene terephthalate (PET), which can be used in, for example, synthetic fibers, beverage, food and other liquid containers, thermoforming applications, and engineered resins.

Embodiments of the process of the present disclosure will now be illustrated by the following non-limiting examples.

EXAMPLES

Example 1

The oxidation of paraxylene is known to proceed stepwise through several intermediates, one of which is an aromatic carboxylic acid (4-CBA) before ending with the desired product, terephthalic acid (TA). The effectiveness of a catalyst for tertiary oxidation of paraxylene (pX) to terephthalic acid (TA) was determined using two metrics: a) the activity, or ability to convert the starting materials to the desired products, and b) the selectivity, or ability to convert the starting material to the desired product without excessive production of byproducts (in this case, products such as benzoic acid, carbon dioxide and carbon monoxide). Conversions of the starting material (be it PX or 4-CBA) are used to report on activity. Selectivity is reported either the yield or benzoic acid or using another useful parameter defined as the ratio (moles CO)/(moles TA), also called burning. In some example embodiments, for an oxidation of pX to TA, one would expect the ratio (moles $CO_x$)/(moles TA) to be in the range 0.1-0.4.

Thirty nine metals were screened in groups of three for catalyzing the oxidation of pX to TA in water to determine their activity and selectivity. Catalysts were identified that were selective, and produced reduced amounts of the undesirable by-product benzoic acid, while also being active, and produced high conversions of pX towards TA. Each of the 39 metal catalysts was evaluated independently, based upon the average yield of benzoic acid in each experiment where the metal was used (regardless of the other two metals in the group of three). The selectivity, reported as benzoic acid yield and shown in Table 1 was the average for all experiments where the catalyst metal occurred, regardless of the other two catalyst metals used in the group of three. High levels of benzoic acid production render catalysts economically unacceptable and therefore selectivity to benzoic acid can be used as the primary screening metric.

TABLE 1

Average percent yield of benzoic acid ($\square$1000) during the oxidation of pX by metal catalysts

| Catalyst Metal | Avg. Benzoic Acid (% $\square$ 1000) |
| --- | --- |
| Pd/C | 6.70 |
| Mo | 2.90 |
| Au | 1.86 |
| Te | 1.36 |
| Ti | 1.35 |
| Ta | 1.16 |
| W | 0.96 |
| Pd | 0.84 |
| Ga | 0.67 |
| V | 0.48 |
| Ru | 0.46 |
| Ge | 0.43 |
| Bi | 0.40 |
| Nb | 0.38 |
| Sb | 0.35 |
| Pt/C | 0.32 |
| Re | 0.31 |
| Au/C | 0.30 |
| Rh | 0.20 |
| In | 0.20 |
| Pt | 0.16 |
| Cr | 0.12 |
| Fe | 0.12 |
| Ir/C | 0.09 |
| Cu | 0.08 |
| Ru/C | 0.07 |
| La | 0.06 |
| Ag | 0.05 |
| Ce | 0.05 |
| Ir | 0.04 |
| Sn | 0.04 |
| Co | 0.04 |
| Zr | 0.04 |
| Zn | 0.02 |
| Mn | 0.01 |
| Ni | 0.01 |

Table 1 shows that Pd/C catalysts and Mo-containing catalysts exhibited low selectivity, and consistently produced high levels of the undesirable byproduct benzoic acid. Other metals (Au, Te, Ti, Ta, W, Pd) produced average levels of benzoic acid. Another group of metals (Ga, V, Ru, Ge, Bi, Nb, Sb, Pt/C, Re, Au/C) were more selective towards TA, and produced below average yields of benzoic acid.

In a second analysis, each metal pair was evaluated independently, A subset of experiments was extracted where two metals, M and M' appeared as a pair, regardless of the identity of the third metal. The average conversion and benzoic acid yield for the most active and selective twenty catalyst pairs are shown in Table 2 below:

TABLE 2

Average conversion and yield of benzoic acid ($\square$1000) during the oxidation of pX to TA

| M | M' | Average % Conversion | Average % Benzoic Acid (×1000) |
| --- | --- | --- | --- |
| Ru/C | Ge | 34.6 | 0 |
| Ru/C | Nb | 33.7 | 0 |
| Ru/C | Mo | 33.6 | 0 |
| Ru | Au/C | 32.6 | 0 |
| Ru/C | Sn | 32.1 | 0 |
| Ru/C | Sb | 31.9 | 0 |
| Ru/C | Fe | 31.6 | 0 |
| Ru/C | Ti | 30.6 | 0 |
| Ru/C | Ag | 28.9 | 0.07 |
| Ru/C | Ta | 28.0 | 0 |
| Ru/C | W | 27.7 | 0 |

TABLE 2-continued

Average conversion and yield of benzoic acid
($\square$1000) during the oxidation of pX to TA

| M | M' | Average % Conversion | Average % Benzoic Acid (×1000) |
|---|---|---|---|
| Ru/C | Au | 27.4 | 0.16 |
| Ru/C | Bi | 27.1 | 0 |
| Ru/C | Re | 27.1 | 0.13 |
| Ru/C | Pb | 25.7 | 0 |
| Ru/C | Sc | 25.4 | 0 |
| Ru/C | Cr | 25.2 | 0 |
| Ru/C | Ce | 25.2 | 0 |
| Ru/C | Te | 24.3 | 0 |

As shown in Table 2, ruthenium catalysts exhibited both activity (20-40 mol % conversion) and selectivity (near 0 mol % benzoic acid) for the conversion of pX.

Table 3 below shows the average conversion and benzoic acid yield for the best performing ten catalyst pairs, excluding pairs containing ruthenium. These catalyst pairs were selective, but not as active as the Ru-containing catalysts.

TABLE 3

Average conversion and yield of benzoic acid during the oxidation of pX for two-metal catalysts containing no ruthenium

| M | M' | Average Conversion (mol %) | Average Benzoic Acid (mol % × 1000) |
|---|---|---|---|
| Au/C | Sc | 18.2 | 0 |
| Pt/C | Te | 16.3 | 0 |
| Au/C | Ta | 15.3 | 0 |
| Ir/C | Ce | 13.8 | 0 |
| V | Nb | 12.5 | 0 |
| Ir/C | Co | 12.4 | 0 |
| Au/C | Cu | 12.2 | 0 |
| Ir/C | V | 11.7 | 0 |
| V | Ge | 11.6 | 0 |
| V | Ga | 11.5 | 0 |

As shown in Tables 1-3 above, the Ru/C catalyst family provided the most active oxidation of pX in water with correspondingly good selectivity, as judged by low yields of benzoic acid. Other heterogeneous catalysts, including the Au/C, Pt/C, and Ir/C families, give moderately good conversions of pX with low production of benzoic acid.

Example 2

Selective removal of small amounts of 4-CBA (a few thousand ppm) from crude TA is important in the production of high quality purified terephthalic acid. In practice, the 4-CBA co-crystallizes along with the TA, making removal difficult. This removal is typically performed by chemically reducing the 4-CBA with hydrogen gas over a catalyst, rather than by oxidation. Severe oxidations can lead to high burning (high (mol COx)/mol pX)) and high levels of byproducts such as benzoic acid. A number of Ru-based heterogeneous catalysts identified in Example 1 above were evaluated for aqueous oxidation of 4-CBA in crude TA.

Oxidations were carried out using 50 mL titanium autoclaves with crude TA concentrations set at 2% w/w, which is the saturation concentration at the reaction temperature, T=210° C. Crude TA was obtained from BP Amoco Chemical Company, Decatur, Ala., with [4-CBA]=3663 ppm. Ru was added either as the metal on carbon or as the metal on rutile titania. Ir was added as Aldrich 5% iridium on carbon. Other metal ions were added as acetate or acetylacetonate (acac) salts. To limit burning reactions that reduce selectivity and produce CO, $CO_2$ and benzoic acid, 1% $O_2$ was used, rather than the customary 8% $O_2$ usually used for pX oxidations (this was still a 100 times stoichiometric excess for the 4-CBA available). The reaction time was set to 10 minutes. Four CoMnBr catalyst baseline samples were added for comparison.

Under the conditions chosen, the CoMnBr baseline catalysts converted little or no 4-CBA in the crude TA samples, while oxidations carried out using Ru/C tended to have high burning, which may have been due to combustion of the carbon support. Oxidations carried out using Ru on rutile had both good activity for the conversion of 4-CBA and good selectivity, as judged by low burning and benzoic acid yield. The most active and selective catalysts were tabulated in Table 4 below.

Table 4 includes three measures of selectivity: (1) the yield of the undesirable byproduct and benzoic acid; (2) the maximum % of TA burned during the oxidation (an estimate of the maximum because these batch reactions did not evolve $CO_2$ at a constant rate, thus the maximum $CO_x$ evolution rate was selected and applied to the entire tertiary oxidation time; and (3) the maximum burning ratio, (mol COx)/(mol TA) during the oxidation. This ratio is a common measure of burning during oxidations that produce TA. The cost of burning in oxidation was calculated using estimated historical prices of $860/te pX.

TABLE 4

Results for the oxidation of 4-CBA in crude TA
([4-CBA]$_0$ = 3663 ppm) using ruthenium-based catalysts

| Catalyst | Residual [4-CBA] (ppm) | Yield benzoic acid (%) | Maximum TA burned | Maximum (mol COx)/ (mol TA) |
|---|---|---|---|---|
| Ru/rutile + Sb | 272 | 0.00 | 0.16% ($1.44/te) | 0.0128 |
| Ru/rutile + Mo, Pb | 69 | 0.07 | 0.27% ($2.43/te) | 0.0216 |
| Ru/rutile + Mo, In | 125 | 0.13 | 0.34% ($3.06/te) | 0.0272 |
| Ru/rutile | 113 | 0.00 | 0.36% ($3.24/te) | 0.0288 |
| Ru/C + In, Au | 70 | 0.35 | 0.40% ($3.60/te) | 0.032 |
| Ru/rutile + Mo, Nb | 265 | 0.26 | 0.59% ($5.31/te) | 0.0472 |
| Ru/C + Mo, Nb | 0 | 0.71 | 0.64% ($5.76/te) | 0.0512 |
| CoMnBr (avg.) | 3527 | 0.06 | 0.18% ($1.26) | 0.0147- |

Based on the results in Table 4, the RuSb and RuMo families provided the best overall performance. They exhibited the highest activity, converting 90+% of 4-CBA to TA, while also demonstrating high selectivity as demonstrated by the low yields of benzoic acid, and burning less than 1% of the TA ($1-$6/te TA).

Example 3

Oxidizing the residual 4-CBA in crude TA (typically [4-CBA]>3000 ppm) requires a small amount of oxygen compared to the oxidation of pX to TA. Stoichiometrically, the oxidation of the residual 4-CBA in a crude TA feed (typically [4-CBA]>3000 ppm) only requires about 0.3% of the oxygen required for the oxidation of pX and should therefore require lower amounts of oxidant than the standard 8% O2 feed used for PX production. Stoichiometric amounts of either air or hydrogen peroxide to oxidize 4-CBA were used. Oxidations of 4-CBA were carried out in a 78 mL Ti batch reactor as shown in Table 5. In a typical reaction, 4-CBA (0.12 g, 0.8 mmol), Ru/rutile catalyst, distilled water (30 g, purged with nitrogen) and 2% $H_2O_2$ (1.4 g, 0.8 mmol) or air (0.8 mmol $O_2$) were loaded into the reactor. The reactor was pressurized with 200 psi nitrogen, and then heated to 290° C. while mixing at 300 rpm for five minutes. After cooling the reactor the gases were analyzed by gas chromatography (GC) and the total products analyzed by liquid chromatography. Results for the oxidation of 4-CBA by $O_2$ or $H_2O_2$ over the Ru/rutile catalyst in water at T=290° C. are shown in Table 5 below.

TABLE 5

Oxidations of 4-CBA using either $O_2$ or $H_2O_2$ Ru/rutile catalysts

| Exp. # | eq. $H_2O_2$ | eq. $O_2$ | Mass Catalyst (g) | Yield Benzoic Acid (%) | Conversion of 4-CBA (%) | (mol COx)/ (mol 4-CBA) |
|---|---|---|---|---|---|---|
| 1 | 1.03 | 0 | 0 | 0.25 | 81 | 0.0041 |
| 2 | 1.03 | 0 | 0.1 | 0.23 | 74 | 0.0026 |
| 3 | 1.03 | 0 | 0.2 | 0.20 | 81 | 0.0015 |
| 4 | 1.03 | 0 | 0.4 | 10.5 | 96 | 0.0042 |
| 5 | 0 | 0.52 | 0 | 0.50 | 66 | 0.0032 |
| 6 | 0 | 0.52 | 0.1 | 1.0 | 77 | 0.0021 |
| 7 | 0 | 0.52 | 0.2 | 0.25 | 87 | 0.0017 |
| 8 | 0 | 0.52 | 0.4 | 12.3 | 93 | 0.0039 |
| Rutile | 1.03 | 0 | 0.5 | 0 | 69 | 0.0110 |
| Rutile | 0 | 0.50 | 0.5 | 0 | 67 | 0.0042 |

Figure 2:
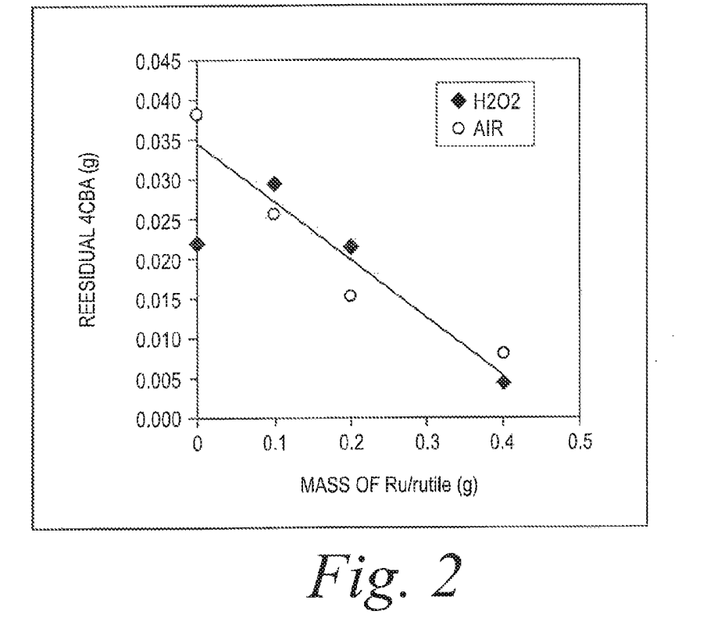
FIG. 2 is a plot of residual 4-CBA remaining after the oxidation of 4-CBA under the conditions outlined in Table 5 and Example 3.

FIG. 2 shows the residual 4-CBA remaining after the oxidation steps outlined above in Table 5.

Figure 3:
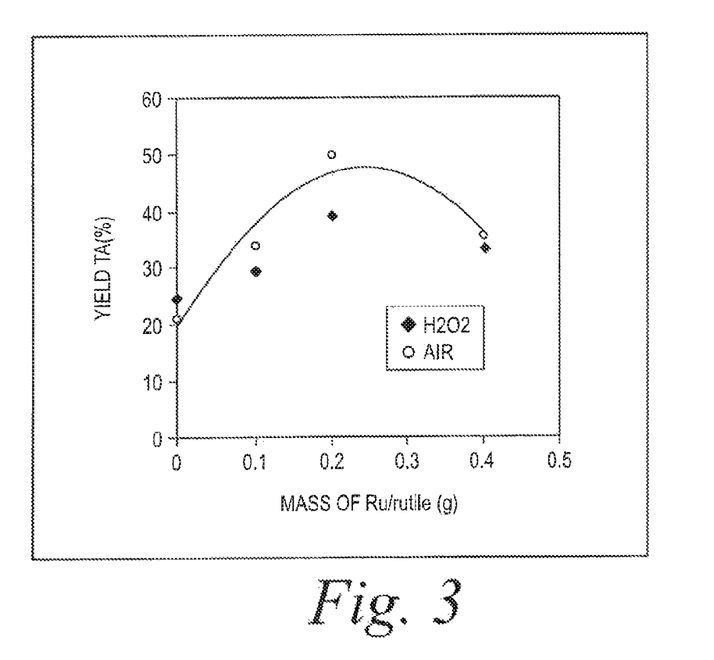
FIG. 3 is a plot showing TA yield as a function of catalyst mass during the oxidation of 4-CBA under the conditions in Table 5 and Example 3.

FIG. 3 shows the TA yield from the oxidations outlined in Table 5. The maximum TA yield is reached near 0.2 g Ru/rutile. After this point, TA yield is lost due to conversion of some products to byproducts like $CO_x$ and benzoic acid.

Figure 4:
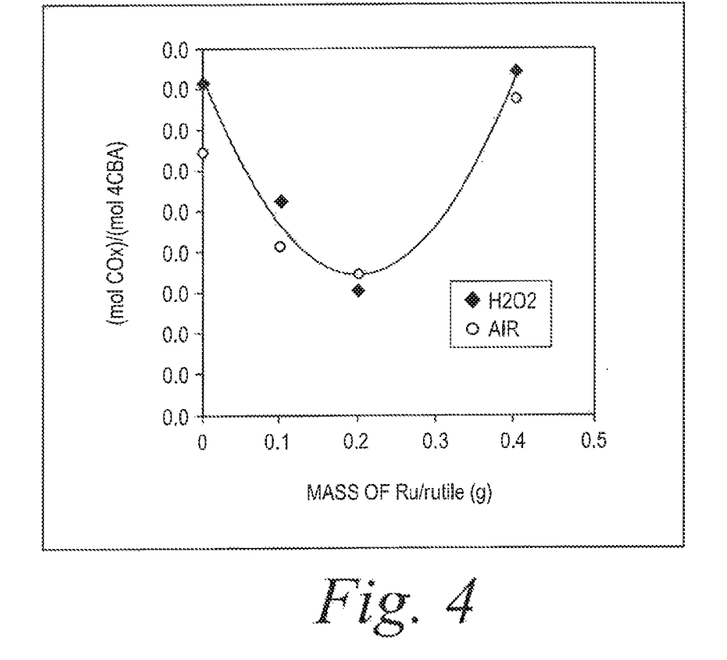
FIG. 4 is a plot showing Concentration of $CO_2$ in the overhead gas as a function of catalyst mass during the oxidation of 4-CBA under the conditions in Table 5 and Example 3.

FIG. 4 shows that the $CO_2$ concentration in the off-gas reaches a desirable minimum at the same 0.2 g of catalyst. The CO concentration shows the same trend. This corresponds with the maximum TA yield in FIG. 4.

Figure 5:
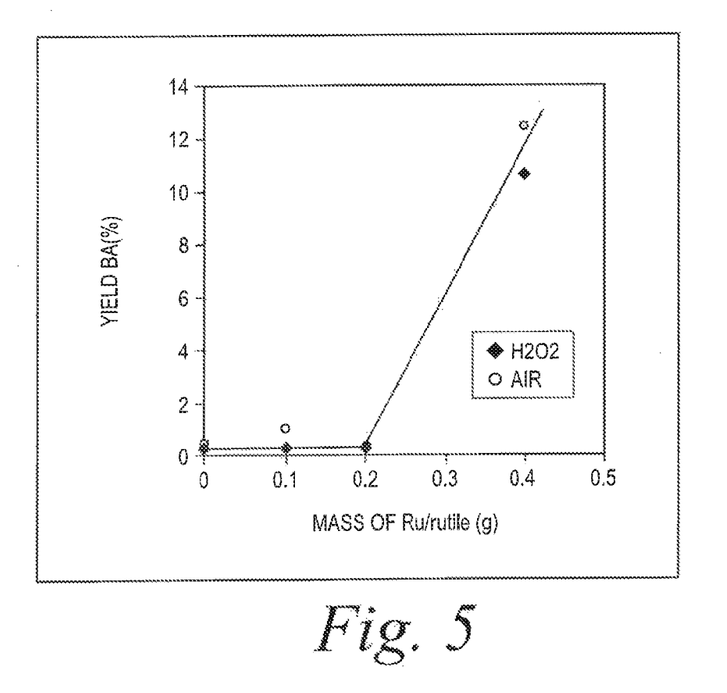
FIG. 5 is a plot of benzoic acid yield as a function of catalyst mass during the oxidation of 4-CBA under the conditions of Table 5 and Example 3.

Benzoic acid yield varies with catalyst loading as shown in FIG. 5. Benzoic acid yield is low until catalyst loading reaches 0.4 g at which point it increases drastically.

Two additional runs were performed using only the rutile support. The rutile support is rather poor at oxidizing 4-CBA to TA under the conditions chosen here. The burning to $CO_2$ is quite high for the rutile support, indicating that the rutile support may not be inert.

Example 4

The examples above show that 4-CBA in crude TA ([4-CBA]=3663 ppm) can be oxidized using selective and active catalysts. The oxidation of 4-CBA in crude TA can also be accomplished using active and selective catalysts, where [4-CBA]>3663 ppm. Such a catalyst would give greater flexibility in operating both the primary oxidation reactor, and the purification reactor. To demonstrate the effectiveness of catalysts for oxidizing 4-CBA in crude TA, where [4-CBA]>3663 ppm, a synthetic crude TA was prepared by mixing purified TA and 4-CBA such that [4CBA]=10,000 ppm in the resulting mixture. Ruthenium on rutile (0.5 g) was loaded into a 78 mL titanium autoclave reactor. Purified TA (6 g, [4-CBA]=0 ppm) and 4-CBA (0.060 g, 0.4 mmol) were added to the reactor along with water (30 g) and finally, just before sealing the reactor, 2% hydrogen peroxide (0.70 g, 0.4 mmol). The reactor was purged 2× with nitrogen, then pressurized with 200 psi nitrogen, and heated to T=290° C.; t=5 minutes with mixing. After the reaction, the gases were analyzed for $CO_x$ using gas chromatography and the total product analyzed by liquid chromatography. The experiment was repeated with 1.4 g (0.8 mmol, 2 eq) peroxide and repeated again with 2.1 g (1.2 mmol, 3 eq) peroxide.

Table 6 below shows the oxidation of 4-CBA in synthetic crude TA using Ru/rutile catalyst and variable quantities of $H_2O_2$.

TABLE 6

Results for the oxidation of 4-CBA with $H_2O_2$ and Ru/rutile catalyst

| Equivalents of $H_2O_2$ | Conversion of 4-CBA (%) | Yield Benzoic Acid (%) | (mol COx)/ (mol TA) |
|---|---|---|---|
| 1.04 | 46.7 | 0 | 0.0024 |
| 2.10 | 55.5 | 0 | 0.0062 |
| 2.06 | 54.5 | 0 | 0.0066 |
| 3.09 | 61.8 | 0 | 0.0074 |

Figure 6:
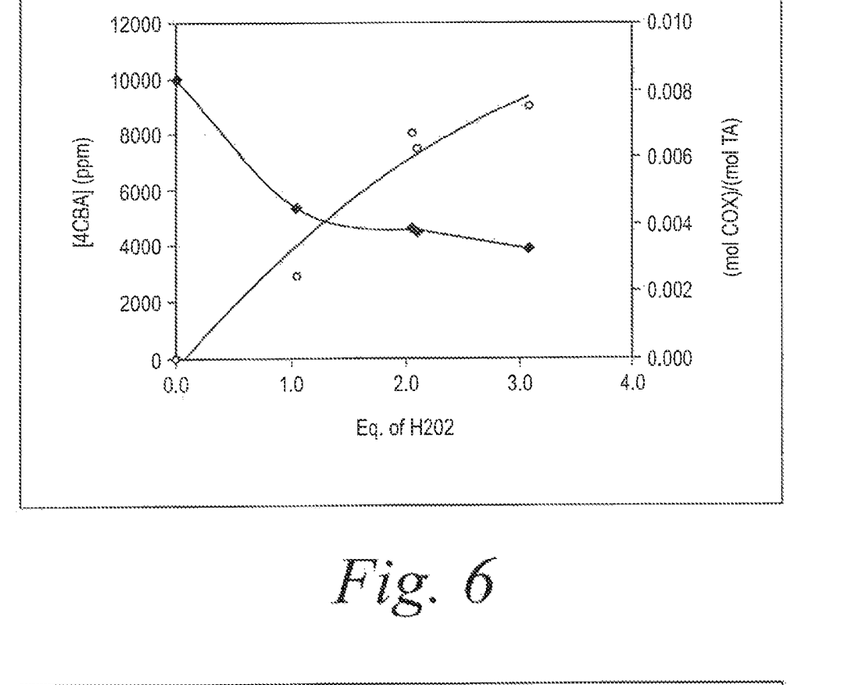
FIG. 6 is a plot of the oxidation of 4-CBA in TA using Ru/rutile and variable quantities of $H_2O_2$ using the data of Table 6.
Figure 7:
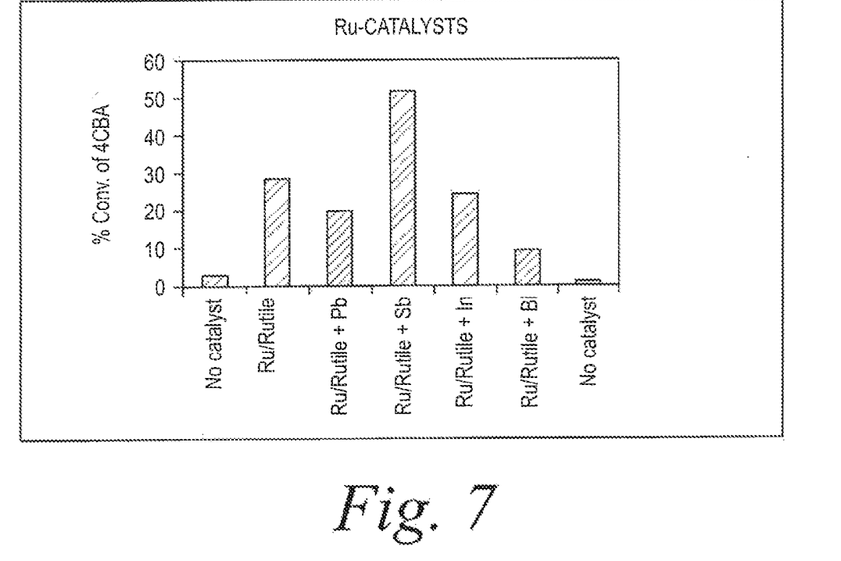
FIG. 7 is a plot showing an analysis of the oxidation of 4-CBA in CTA by $H_2O_2$ as shown in Table 7 and Example 5.

Data from Table 6 were plotted as shown in FIG. 6. The results plotted in FIG. 7 show that the Ru/rutile catalyst is capable of oxidizing substantial quantities of 4-CBA in synthetic crude TA containing [4-CBA]=3000-10,000 ppm without significantly adding to burning or benzoic acid production.

Example 5

The Ru/rutile catalyst was improved by the addition of metal salts that were identified in Table 4, above. These catalyst combinations were shown to increase activity and selectivity of the basic Ru/rutile catalyst at T=210° C. with stoichiometric excess of oxygen. Their effectiveness was demonstrated at T=290° C., using stoichiometric amounts of hydrogen peroxide. Ruthenium on rutile (0.5 g) was loaded into a 78 mL titanium autoclave reactor along with various metal acetate salts Crude TA (6 g, [4-CBA]=3663 ppm) was added to the reactor along with water (30 g) and finally, just before sealing the reactor, 2% hydrogen peroxide (0.25 g). The reactor was purged 2 times with nitrogen, then heated with mixing (T=290° C.; t=5 minutes, 200 psi nitrogen). After the reaction, the overhead gases were analyzed by GC and the total product was analyzed by LC (Table 7).

Table 7 shows an analysis of the oxidation of 4-CBA (3663 ppm) in crude TA by hydrogen peroxide at T=290° C.

TABLE 7

Results for the oxidation of crude TA containing 4-CBA ([4-CBA]$_0$ = 3663 ppm) hydrogen peroxide using Ru/rutile and metal acetate catalysts. T = 290° C.

| Catalyst | Conversion of 4-CBA (%) | (mol COx)/ (mol TA) | Yield Benzoic Acid (%) |
|---|---|---|---|
| None | 3.1 | 0.0037 | 0.047 |
| Ru/Rutile | 28.6 | 0.0012 | 0.047 |
| Ru/Rutile + Pb | 19.9 | 0.0016 | 0.055 |
| Ru/Rutile + Sb | 51.5 | 0.0003 | 0.047 |
| Ru/Rutile + In | 24.0 | 0.0013 | 0.043 |
| Ru/Rutile + Bi | 9.0 | 0.0019 | 0.048 |
| None | 0.7 | 0.0004 | 0.055 |

The results of the runs reported in Table 7 are plotted in FIG. 7. As shown in FIG. 7, in the absence of catalyst, conversion of 4-CBA was very low (<5%). Ru-catalysts improved the conversion of 4-CBA to TA while burning and benzoic acid remained very low. The Ru/rutile Sb catalyst outperformed the baseline Ru/rutile catalyst in terms of 4-CBA conversion and burning.

Various embodiments of the invention have been described. These and other embodiments are within the scope of the following claims.

The invention claimed is:

1. A process, comprising:
   (a) oxidizing a feedstock comprising an alkyl aromatic compound to form a first crude aromatic carboxylic acid reaction product;
   (b) oxidizing the first crude aromatic carboxylic acid reaction product in one or more sequential reaction mixtures to form a second crude aromatic carboxylic acid reaction product, wherein the second crude aromatic carboxylic acid reaction product comprises 3000 ppm by weight (ppmw) to 10,000 ppmw of aldehyde intermediate reaction products;
   (c) contacting an aqueous reaction mixture comprising the second crude aromatic carboxylic acid reaction product with an oxygen source in the presence of an oxidation catalyst comprising at least one of Ru, Au, Pt, Ir and V, and oxides, alloys, salts and mixtures thereof, to form a third crude aromatic carboxylic acid reaction product, wherein the second crude aromatic carboxylic acid reaction product comprises 3000 ppmw to 6,000 ppmw of aldehyde intermediate reaction products; and
   (d) purifying the third crude aromatic carboxylic acid reaction product with hydrogen to form purified aromatic carboxylic acid, wherein the purified aromatic carboxylic acid has less than 100 ppmw aldehyde intermediate reaction products.

2. The process of claim 1, wherein the oxygen source comprises $H_2O_2$.

3. The process of claim 1, wherein the oxidation catalyst comprises Ru, oxides, alloys, salts and mixtures thereof provided on a support selected from alumina, ceria, zirconia, silica, titania or mixtures thereof.

4. The process of claim 1, wherein the oxidation catalyst comprises at least one of Ru, oxides, alloys, salts and mixtures thereof, and at least one of Mo, Ga and In, and oxides, alloys, salts and mixtures thereof.

5. The process of claim 1, wherein the oxidation catalyst comprises Au and, oxides, alloys, salts and mixtures thereof, and at least one of Sc, Ta or Cu, Pt or Te, and oxides, alloys, salts and mixtures thereof.

6. The process of claim 1, wherein the oxidation catalyst comprises Ir and oxides, alloys, salts, and mixtures thereof, at least one of Ce, Co or V, and oxides, alloys, salts and mixtures thereof.

7. The process of claim 1, wherein the oxidation catalyst comprises V and oxides, alloys, salts, and mixtures thereof, at least one of Nb, Ge, and Ga, and oxides, alloys, salts and mixtures thereof.

8. The process of claim 1, wherein the oxidation catalyst is on a support selected from the group consisting of alumina, silica, zirconia, titania, silicon carbide, carbon, rutile and combinations thereof.

9. The process of claim 1, wherein the oxidation catalyst comprises Ru on a carbon or a rutile support.

10. The process of claim 1, wherein the oxidation catalyst comprises Ru on a rutile support and Sb, and oxides, alloys, salts and mixtures thereof; Ru on a rutile support and at least one of Mo and Pb, and oxides, alloys, salts and mixtures thereof; Ru on a rutile support and at least one of Mo and In, and oxides, alloys, salts and mixtures thereof; Ru on a carbon support and at least one of In and Au, and oxides, alloys, salts and mixtures thereof; or Ru on a rutile support and at least one of Mo and Nb, and oxides, alloys, salts and mixtures thereof.

11. The process of claim 1, wherein the solution is at a temperature of 275° C. to 300° C.

12. The process of claim 1, further comprising forming the crude aromatic carboxylic acid by oxidizing an alkyl aromatic compound.

13. The process of claim 1, wherein the alkyl aromatic compound is paraxylene and the purified aromatic carboxylic acid is purified terephthalic acid.

* * * * *